(12) United States Patent
Kang

(10) Patent No.: US 12,096,190 B2
(45) Date of Patent: Sep. 17, 2024

(54) APPARATUS AND METHOD FOR PROTECTING DENTAL PATIENT HEARING THROUGH NOISE REDUCTION

(71) Applicant: HEALING SOUND CO., LTD., Seoul (KR)

(72) Inventor: Jun Gu Kang, Seoul (KR)

(73) Assignee: HEALING SOUND CO., LTD., Seoul (KR)

( * ) Notice: Subject to any disclaimer, the term of this patent is extended or adjusted under 35 U.S.C. 154(b) by 177 days.

(21) Appl. No.: 17/797,107

(22) PCT Filed: Jul. 9, 2020

(86) PCT No.: PCT/KR2020/009016
§ 371 (c)(1),
(2) Date: Aug. 3, 2022

(87) PCT Pub. No.: WO2022/010011
PCT Pub. Date: Jan. 13, 2022

(65) Prior Publication Data
US 2023/0055191 A1     Feb. 23, 2023

(51) Int. Cl.
*G10K 11/178*     (2006.01)
*A61B 5/00*      (2006.01)
(Continued)

(52) U.S. Cl.
CPC ........... *H04R 3/007* (2013.01); *A61B 5/0205* (2013.01); *A61B 5/02055* (2013.01);
(Continued)

(58) Field of Classification Search
CPC ........... H04R 1/1083; G10K 2210/116; G10K 2210/1081
See application file for complete search history.

(56) References Cited

U.S. PATENT DOCUMENTS

| | | | |
|---|---|---|---|
| 9,609,423 B2* | 3/2017 | Montazemi | H04R 1/1083 |
| 2011/0193380 A1* | 8/2011 | Yamada | H04R 5/023 |
| | | | 297/217.4 |

(Continued)

FOREIGN PATENT DOCUMENTS

| KR | 10-2003-0035479 A | 5/2003 |
|---|---|---|
| KR | 10-2008-0023479 A | 3/2008 |

(Continued)

OTHER PUBLICATIONS

International Search Report for PCT/KR2020/009016 mailed Apr. 8, 2021 from Korean Intellectual Property Office, 6 pages.

*Primary Examiner* — Ping Lee
(74) *Attorney, Agent, or Firm* — Revolution IP, PLLC

(57) ABSTRACT

The present invention provides an apparatus for protecting dental patient hearing through noise reduction, the apparatus comprising: a main body portion provided in a form that can be mounted on both ears of a user; a microphone module that is provided on one side of the main body portion and collects external sound signals generated from the outside; a noise filter module that is built in the main body portion and filters the external sound signals to block or reduces noise signals included in the external sound signals; and a speaker module that is built in the main body portion and provided on the other side of the main body portion corresponding to the ears of the user, and that outputs sound signals filtered by the noise filter module.

16 Claims, 5 Drawing Sheets

(51) Int. Cl.
*A61B 5/0205* (2006.01)
*A61B 5/024* (2006.01)
*G06F 3/16* (2006.01)
*H04R 1/10* (2006.01)
*H04R 3/00* (2006.01)
*A61B 5/01* (2006.01)

(52) U.S. Cl.
CPC ............ *A61B 5/7203* (2013.01); *G06F 3/165* (2013.01); *G10K 11/17823* (2018.01); *G10K 11/17873* (2018.01); *G10K 11/17885* (2018.01); *H04R 1/1083* (2013.01); *A61B 5/01* (2013.01); *A61B 5/02438* (2013.01); *G10K 2210/116* (2013.01)

(56) References Cited

U.S. PATENT DOCUMENTS

| | | | |
|---|---|---|---|
| 2014/0044269 A1* | 2/2014 | Anderson | H04R 1/1083 381/57 |
| 2015/0304761 A1 | 10/2015 | Montazemi et al. | |
| 2018/0005622 A1* | 1/2018 | Kyllönen | H04R 1/1016 |
| 2020/0005766 A1 | 1/2020 | Kim | |
| 2020/0128317 A1* | 4/2020 | Feldman | H04R 1/083 |
| 2020/0135163 A1* | 4/2020 | Lovitt | G10K 11/17837 |
| 2022/0387747 A1* | 12/2022 | Kang | G06F 3/165 |

FOREIGN PATENT DOCUMENTS

| | | |
|---|---|---|
| KR | 10-1958839 B1 | 7/2019 |
| KR | 10-2019-0103080 A | 9/2019 |
| KR | 10-2138772 B1 | 7/2020 |

\* cited by examiner

APPARATUS AND METHOD FOR PROTECTING DENTAL PATIENT HEARING THROUGH NOISE REDUCTION

TECHNICAL FIELD

The present invention relates to an apparatus and method, whereby patient hearing is protected by reducing noise generated during dental treatment.

BACKGROUND ART

It is very significant to create a comfortable and comfortable environment for treating patients. A quiet environment may be provided to a patient depending on how a disease is treated, whereas in the dental field, sharp and high-frequency noise generated during a treatment process may create discomfort or fear in the patient. However, measures to protect patients exposed to such high-frequency noise are insufficient.

Meanwhile, an active noise control technology is a technology, whereby ambient noise is received through a microphone separately attached to a headphone or an earphone and destructive interference for cancelling the noise is generated in a noise cancelling circuit, thereby blocking noise. In the related art, the active noise control technology is applied to the headphone or earphone and thus used only for multimedia viewing, and the development of technology to be applied to other environments has not been largely accomplished.

DETAILED DESCRIPTION OF THE INVENTION

Technical Problem

The present invention provides an apparatus and method for protecting dental patient hearing, whereby the apparatus for protecting dental patient hearing is implemented in a structure in which a dental patient wears the apparatus on the ears and external sound is collected through a microphone and then sound from which high-frequency noise is blocked, is transmitted to the dental patient through filtering.

The present invention provides an apparatus and method for protecting dental patient hearing, whereby an environment where the dental patient receives treatment while hearing multimedia being used, is provided.

Technical Solution

According to an aspect of the present invention, there is provided an apparatus for protecting dental patient hearing, the apparatus including: a main body portion provided in a form that can be mounted on both ears of a user; a microphone module that is provided on one side of the main body portion and collects external sound signals generated from the outside; a noise filter module that is built in the main body portion and filters the external sound signals to block or reduces noise signals included in the external sound signals; and a speaker module that is built in the main body portion and provided on the other side of the main body portion corresponding to the ears of the user, and that outputs sound signals filtered by the noise filter module.

According to another aspect of the present invention, there is provided a method for protecting dental patient hearing, the method including: an apparatus providing operation in which an apparatus for protecting dental patient hearing, the apparatus including a main body portion provided in a form that can be mounted on both ears of a user, a microphone module that collects an external sound signal generated from the outside, a noise filter module that is built in the main body portion and filters the external sound signals to block or reduces noise signals included in the external sound signals, and a speaker module that is built in the main body portion and provided on the other side of the main body portion corresponding to the ears of the user, and that transmits sound signals filtered by the noise filter module, is provided to a patient; a content signal outputting operation in which a first sound signal received from a multimedia storage device spaced from the apparatus for protecting dental patient hearing is output through the speaker module; an output controlling operation in which, when the apparatus for protecting dental patient hearing receives a second sound signal above a preset sound level, an output of the first sound signal is stopped or a volume of the first sound signal is reduced by a preset value; and a nose reduction operation in which, when sound above a preset frequency is received through the microphone module, sound above the preset frequency is blocked or reduced through filtering of the noise filter module and output to the speaker module.

Effects of the Invention

According to the present invention, an apparatus for protecting dental patient hearing is implemented in a structure in which a dental patient wears the apparatus on the ears, and external sound is collected through a microphone and then sound from which high-frequency noise is blocked, can be transmitted to the dental patient through filtering.

In addition, according to the present invention, an environment where the dental patient receives treatment while hearing multimedia being used, can be provided.

MODE OF THE INVENTION

Hereinafter, the configuration and operation of embodiments of the present invention will be described in detail with reference to the accompanying drawings.

Figure 1:
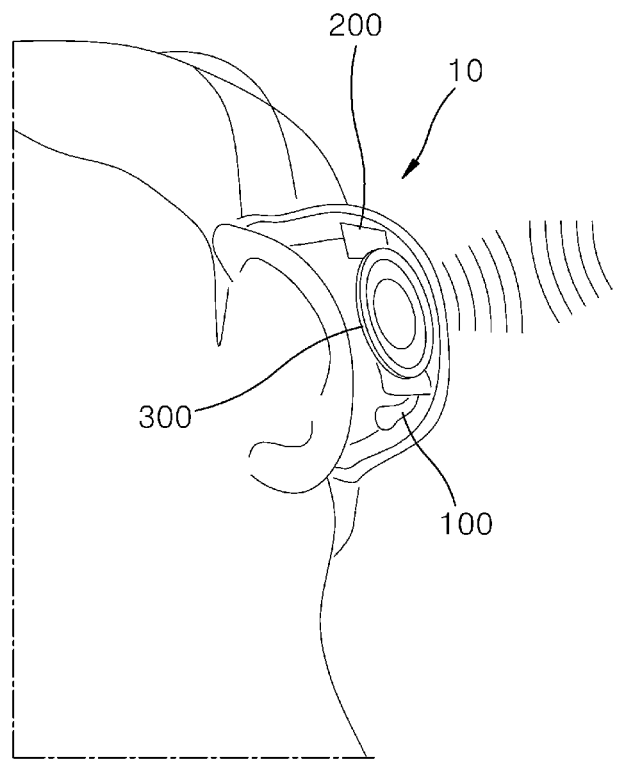
FIG. 1 is a view schematically illustrating elements of an apparatus for protecting dental patient hearing through noise reduction according to an embodiment of the present invention.

FIG. 1 is a view schematically illustrating elements of an apparatus for protecting dental patient hearing through noise reduction according to an embodiment of the present invention. Referring to FIG. 1, an apparatus 10 for protecting dental patient hearing through noise reduction includes a microphone module 100, a noise filter module 200, and a speaker module 300.

A patient who wears the apparatus 10 for protecting dental patient hearing hears sound from which high-frequency noise is blocked or reduced. The apparatus 10 for protecting dental patient hearing may be worn by a medical staff who treats the patient in addition to the patient.

Here, a main body portion of the apparatus 10 for protecting dental patient hearing may be provided in a form in which the main body portion may be mounted on both ears of the dental patient who is a user. Here, the main body portion may refer to a case. The apparatus 10 for protecting dental patient hearing may be implemented in a headphone type or an earphone type, and because the apparatus 10 for protecting dental patient hearing may be modified in various forms according to the purpose of use and implemented, the shape of the main body portion does not largely limit the scope of the present invention. Thus, as an alternative embodiment, the main body portion may also be implemented in the form of a helmet or in a structure in which the main body portion is inserted into a headrest of a chair.

The microphone module 100 is provided on one side of the main body portion and collects sound signals generated from the outside. Here, the sound signals refer to signals including sound including at least one of human voice, external noise, and sound of content played through multimedia.

The noise filter module 200 is built in the main body portion, filters sound signals collected from the outside through the microphone module 100, so that sounds above a preset filtering reference frequency are considered high-frequency noise and are reduced or blocked, and sounds below the filtering reference frequency are provided to the user.

In the present embodiment, it will be described that the noise filter module 200 is implemented by applying a low pass filtering technology, but the present invention is not limited thereto. In the present embodiment, low pass filtering is performed to remove sounds above the filtering reference frequency. For example, the filtering reference frequency may be 3000 Hz, and because mechanical sound used in dentist is generated at a frequency of about 3000 Hz or higher, when this frequency is removed, stress or fear applied to the dental patient may be removed. In the present embodiment, it will be described that the filtering reference frequency is 3000 Hz, however, unlike this, the filtering reference frequency may be different numbers of frequencies (e.g., 3500 Hz or 4000 Hz). Also, the apparatus 10 for protecting dental patient hearing may be configured to select one from among several frequencies as a filtering reference frequency according to the situation and conditions of a hospital, and this also belongs to the scope of the present invention.

In an alternative embodiment, the noise filter module 200 may perform filtering to remove loud noise above a preset filtering reference sound level. This is because too loud noise gives stress to the patient. In the present embodiment, it will be described that the filtering reference sound level is 80 decibel (dB), and the present invention is not limited thereto.

The speaker module 300 is built in the main body portion, is provided at the other side of the main body portion corresponding to the user's ears and outputs filtered sound signals.

In an alternative embodiment, when the speaker module 300 protrudes from the outside of the main body portion, the speaker module 300 may be implemented in various forms that may correspond to various sizes and shapes, or the speaker module 300 may be replaced.

Figure 2:
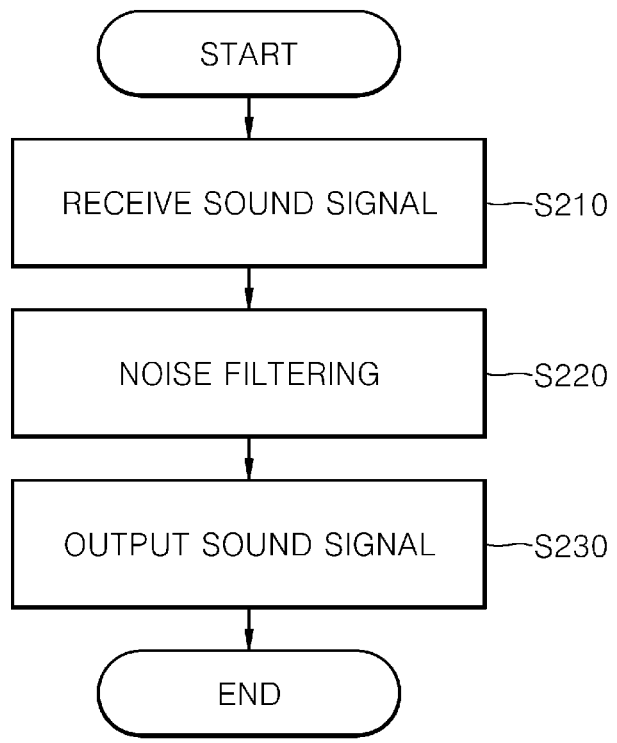
FIG. 2 is a flowchart illustrating a procedure in which noise is reduced by the apparatus for protecting dental patient hearing shown in FIG. 1.

FIG. 2 is a flowchart illustrating a procedure in which noise is reduced by the apparatus for protecting dental patient hearing shown in FIG. 1. When describing a procedure in which noise is reduced with reference to FIG. 2, first, sound signal reception operation (S210) is performed. In sound signal reception operation (S210), sound signals are received through the microphone module 100. In this case, the sound signals received by the microphone module 100 refer to all sounds including noise, and the microphone module 100 receives the sound signals in real time while the apparatus 10 for protecting dental patient hearing operates.

Next, noise filtering operation (S220) is performed. In noise filtering operation (S220), the noise filter module 200 filters the sound signals received in sound signal reception operation (S210) so that sound above the filtering reference frequency or sound above the filtering reference sound level is blocked or reduced.

Next, sound signal outputting operation (S230) is performed. In sound signal outputting operation (S230), the speaker module 200 outputs the sound signals filtered in noise filtering operation (S220). Thus, while the dental patient receives treatment, the dental patient hears sound in which noise is removed or reduced from external sound.

Additionally, content signal outputting operation may be performed. In content signal outputting operation, the main body portion is connected to an external storage device, and a first sound signal received from the external device is output through the speaker module 300 before sound signal reception operation (S210) is performed. This is because the patient wants to hear desired music or content before treatment starts being performed or while treatment is performed. In the present embodiment, the first sound signal refers to content including sound signals stored in the external storage device.

When a second sound signal is received through the microphone module 100 while the main body portion outputs the first sound signal in content signal outputting operation, output of the first sound signal is stopped, or the volume of the first sound signal is reduced by a preset value. In the present embodiment, the second sound signal refers to a sound signal different from the first sound signal with the sound level above a preset decibel. For example, the second sound signal may refer to sound generated from the outside and may be a sound signal such as human conversation voice. For example, while the patient is hearing music, when a dentist says something to the patient, music is stopped or volume is reduced so that the voice of the dentist may be transmitted to the patient. In this case, the patient may relax through music before treatment begins, but communication with the dentist may not be cut off.

Meanwhile, filtering is performed on noise of the second sound signal through the noise filter module 200, and the filtered second sound signal is output through the speaker module 300.

In addition, as an alternative embodiment, because people have different hearing and different recognition rates and the voice of the dentist wearing a mask may be unclear, the time for lowering or stopping the volume of the first sound signal may be customized in advance. For example, when the dentist gives a test voice 'can you hear me?' before starting treatment, the first sound signal may stop or the volume of the first sound signal may be reduced by 30% for a preset period of time (e.g., 3 seconds). Thereafter, according to the patient's response, the preset time may be increased or the volume lowering ratio may be increased, which is performed by inputting a time setting or volume control signal to a separate terminal (e.g., a dentist's smartphone) and by transmitting a control signal corresponding thereto to an apparatus for protecting dental patient hearing. Alternatively, a button for adjusting the preset time and volume may be provided in the apparatus for protecting dental patient hearing itself.

Figure 3:
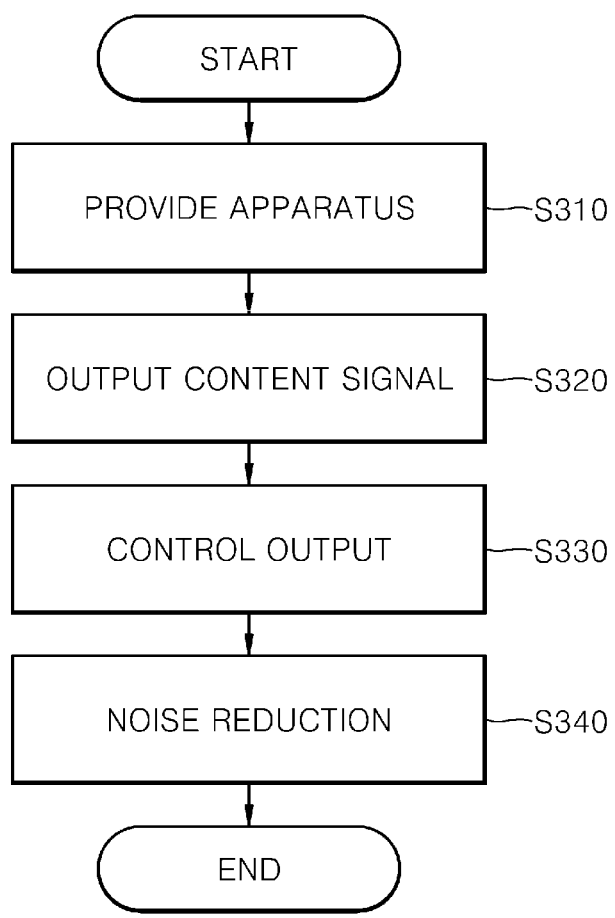
FIG. 3 is a flowchart illustrating a method for protecting dental patient hearing through noise reduction according to an embodiment.

FIG. 3 is a flowchart illustrating a method for protecting dental patient hearing through noise reduction according to an embodiment. The method for protecting dental patient hearing will be described with reference to FIG. 3 as below.

First, apparatus providing operation (S310) in which the apparatus 10 for protecting dental patient hearing is provided to the patient, is performed. In apparatus providing operation (S310), a doctor or a nurse transmits the apparatus 10 for protecting dental patient hearing to the patient so as to wear the apparatus 10 for protecting dental patient hearing before performing treatment.

When the apparatus 10 for protecting dental patient hearing is provided in a medical chair, the patient may find and wear the apparatus 10 for protecting dental patient hearing by himself/herself.

When the apparatus 10 for protecting dental patient hearing is inserted into a headrest of the medical chair and implemented, the patient may receive a noise reduction effect by seating his/her own head on the headrest. In this case, the headrest is implemented in the shape of a wing for surrounding the patient's head, and when the patient seats his/her head on the headrest, the patient may hear sound in which noise output through the speaker module 300 provided in each wing is removed or reduced. In addition, the apparatus 10 for protecting dental patient hearing may be properly coupled to the headrest implemented in a shape in which the patient's convenience may be increased.

In another alternative embodiment, when the apparatus 10 for protecting dental patient hearing is implemented in the form of an earphone, the apparatus 10 for protecting dental patient hearing may be installed to be coupled to an inside/outside of the headrest or the medical chair. In this case, the apparatus 10 for protecting dental patient hearing may be stored in the medical chair at normal times, and the apparatus 10 for protecting dental patient hearing and the medical chair may be connected to each other in a structure of a reel. In this case, the patient may expose the apparatus 10 for protecting dental patient hearing to the outside by pulling the apparatus 10 for protecting dental patient hearing, or by re-pulling the apparatus 10 for protecting dental patient hearing so that the apparatus 10 for protecting dental patient hearing may be automatically rolled and stored in the medical chair.

Next, content signal outputting operation (S320) in which the first sound signal of a multimedia storage device is output through the apparatus 10 for protecting dental patient hearing, is performed. In content signal outputting operation (S320), the main body portion of the apparatus 10 for protecting dental patient hearing is connected to the multimedia storage device via near field communication connection, receives multimedia content from the multimedia storage device and outputs the received multimedia content through the speaker module 300. In the present embodiment, the multimedia storage device refers to a portable terminal device in which multimedia contents such as music or images that an individual prefers are stored at a time when the patient waits before starting a treatment or when a treatment starts. Thus, the first sound signal refers to a sound signal included in music or image contents to be played by the user through his/her own portable terminal.

In an alternative embodiment, when a screen device linked with the apparatus 10 for protecting dental patient hearing is provided, the apparatus 10 for protecting dental patient hearing may play the first sound signal, and an image content corresponding to the first sound signal may be played through the screen device.

Next, when the apparatus 10 for protecting dental patient hearing receives the second sound signal after content signal outputting operation (S320) is performed, output controlling operation (S330) in which the apparatus 10 for protecting dental patient hearing stops the output of the first sound signal or reduces the volume of the first sound signal, is performed. In the present embodiment, the second sound signal refers to a sound signal having a sound level above the preset decibel, and in the present invention, refers to a human conversation voice.

If the patient does not prepare additional multimedia contents in content signal outputting operation (S320), preset white noise may be output to the speaker module 300 by replacing the first sound signal in order to increase the stability of the patient. In this case, when, even in white noise, like in the first sound signal, the second sound signal is received through the microphone module 100, the output of white noise is stopped, or the volume thereof is reduced.

In an alternative embodiment, the second sound signal may be received through an external microphone device connected to the main body portion. The apparatus for protecting dental patient hearing may directly receive the sound signal generated through the external microphone device to output the sound signal to the speaker module 300. For example, when the medical staff including the doctor connects his/her own microphone to the apparatus 10 for protecting dental patient hearing using a technology such as near field communication, and when the medical staff starts conversation with his/her own microphone, the apparatus 10 for protecting dental patient hearing recognizes it and outputs the doctor's words to the speaker module 300.

When the medical staff wears the microphone receiving the second sound signal, the sound may be transmitted to the apparatus 10 for protecting dental patient hearing worn by the patient in the following three embodiments.

Figure 6:
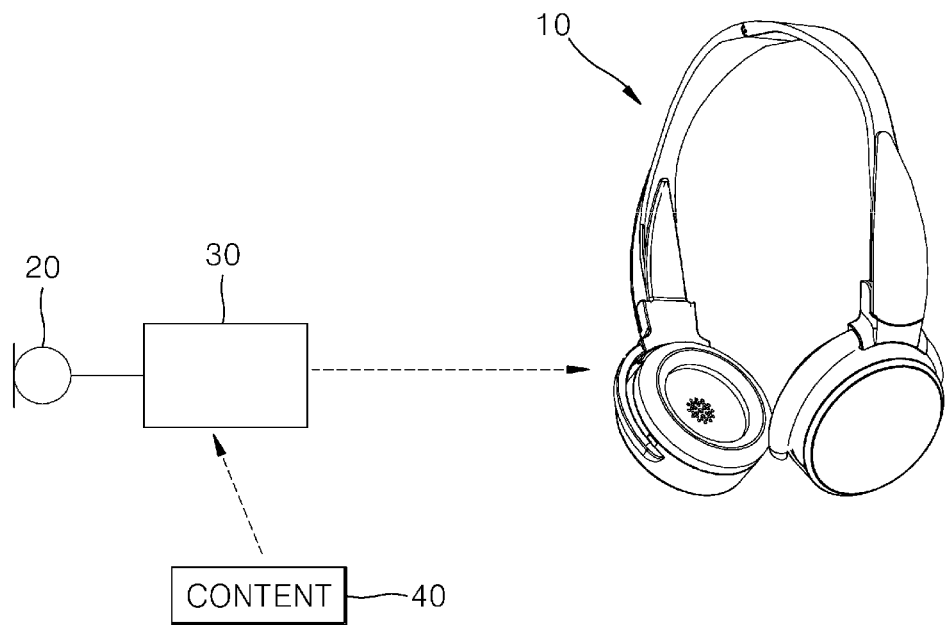
FIG. 6 through 8 are views illustrating three embodiments to transmit sound to an apparatus for protecting dental patient hearing worn by patient.

First, referring to FIG. 6, a transmitter 30 worn by the medical staff together with the microphone 20 is provided, and the transmitter 30 adds the first sound signal transmitted through a communication network such as Bluetooth from an external device 40 with the voice of the medical staff to transmit the first sound signal to the apparatus 10 for protecting dental patient hearing worn by the patient. The microphone 20, the transmitter 30, the external device 40, and the apparatus 10 for protecting dental patient hearing constitute a dental hearing protecting system.

Figure 7:
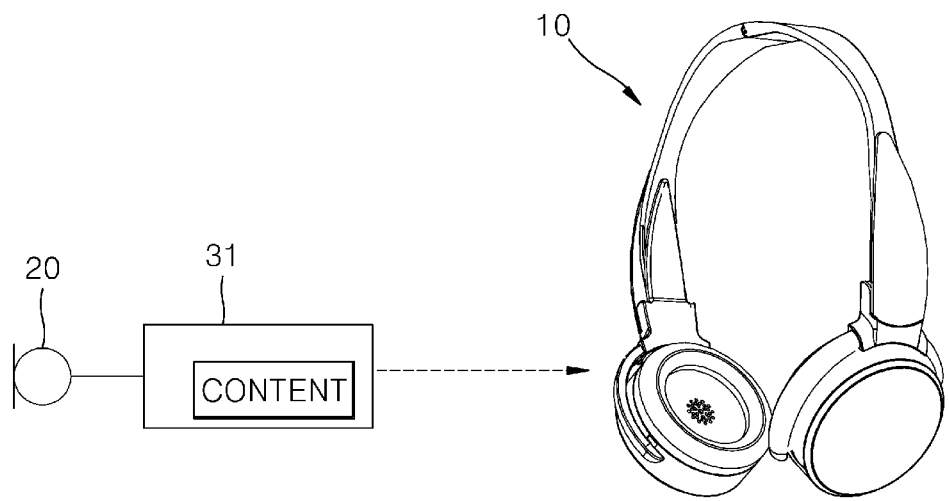

Second, referring to FIG. 7, a transmitter 31 worn by the medical staff together with the microphone 20 is provided, and a plurality of contents corresponding to the first sound signal are stored in the transmitter 31 so that the transmitter 31 adds the voice of the medical staff with the built-in first sound signal to transmit the first sound signal to the apparatus 10 for protecting dental patient hearing worn by the patient. The microphone 20, the transmitter 31, and the apparatus 10 for protecting dental patient hearing constitute a dental hearing protecting system.

Figure 8:
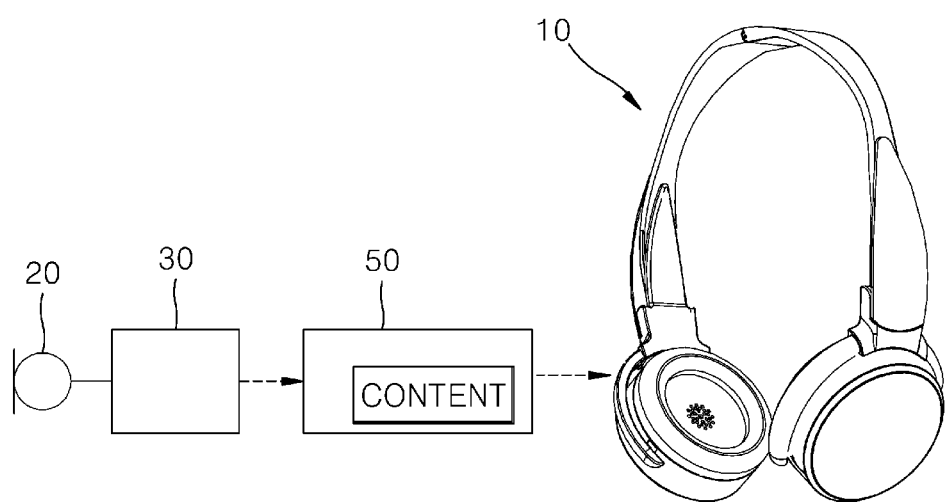

Third, referring to FIG. 8, the transmitter 30 worn by the medical staff together with the microphone 20, and an external terminal device 50, which is connected to communicate between the transmitter 30 and the apparatus 10 for protecting dental patient hearing worn by the patient and in which a plurality of contents corresponding to the first sound signal are stored, are provided, and the external terminal device 50 adds the voice of the medical staff with the built-in first sound signal to transmit the added result to the apparatus 10 for protecting dental patient hearing worn by the patient. Furthermore, a signal processing algorithm such as noise removal is mounted on the transmitter and the external terminal device. The microphone 20, the transmitter 30, the external terminal device 50, and the apparatus 10 for protecting dental patient hearing constitute a dental hearing protecting system.

For effective performance of output controlling operation (S330), an artificial intelligence speech recognition technology may be used. In the artificial intelligence speech recognition technology, sound on each of mechanisms used in the dentist and background sound by department (pediatric dentistry, conservation department, surgical operating room, prosthetics department, orthodontics department, etc.) are collected so that a sound database is established, the collected sound is analyzed according to types and a system may be configured and used to recognize the voice of the medical staff within various noise through artificial intelligence learning.

Next, noise reduction operation (S340) in which sound above a filtering reference frequency or sound above a filtering reference sound level is blocked or reduced by filtering the sound signal received through the microphone module 100 and is output through the speaker module 300, is performed. A procedure in which noise reduction operation (S340) is performed, is roughly the same as the noise reduction procedure described with reference to FIG. 2 and thus, a detailed description thereof will be omitted. In this case, sound above the filtering reference frequency refers to sharp noise generated during the process of treatment or from the outside.

In another embodiment, when a sudden noise situation such as an environment where a baby cries in a pediatric dentist with 120 dB to 130 dB, is detected, the volume of the first sound signal and the volume of the second sound signal may be controlled in response to this. In detail, when there is no second sound signal, the volume of the first sound signal is increased to reduce external noise, and when there is a second sound signal, the volume of the second sound signal is increased so that the voice of the medical staff may be well heard.

Figure 4:
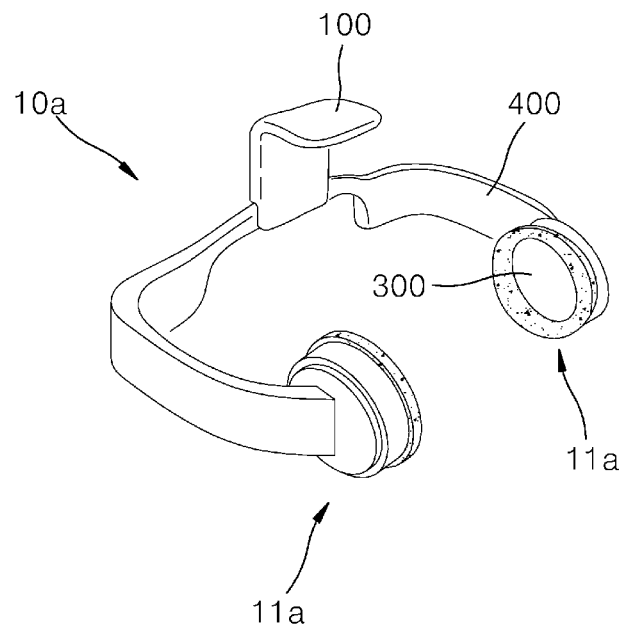
FIG. 4 is a view illustrating an embodiment in which an apparatus for protecting dental patient hearing is implemented in the form of a headphone.
Figure 5:
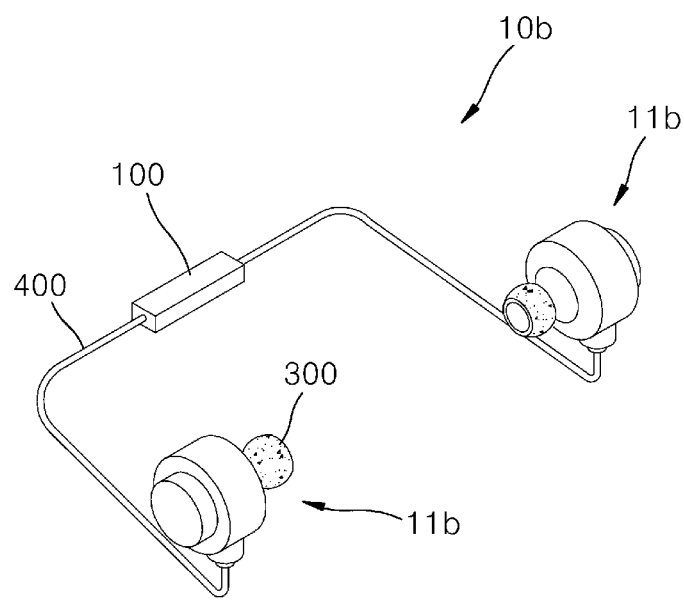
FIG. 5 is a view illustrating an embodiment in which an apparatus for protecting dental patient hearing is implemented in the form of an earphone.

FIG. 4 is a view illustrating an embodiment in which an apparatus for protecting dental patient hearing is implemented in the form of a headphone, and FIG. 5 is a view illustrating an embodiment in which an apparatus for protecting dental patient hearing is implemented in the form of an earphone.

Referring to FIGS. 4 and 5, both a headphone-type apparatus 10a for protecting dental patient hearing and an earphone-type apparatus 10b for protecting dental patient hearing include main body portions 11a and 11b corresponding to both of the ears and a connection portion 400 for connecting the main body portions 11a and 11b.

The microphone module 100 may be mounted on the connection portion 400 so that the microphone module 100 and the speaker module 300 are spaced apart from each other by a preset length. This is because a howling phenomenon that the microphone module 100 and the speaker module 300 are too close to each other and sound output from a speaker is input to the microphone again, is prevented.

In addition, a temperature measuring module is additionally provided inside the main body portions 11a and 11b to measure the body temperature of the human in real time. When temperature (e.g., temperature of 30° C. or less) below a preset value is measured, the current mode is converted into a standby mode in which operations of the apparatuses 10a and 10b are stopped and power consumption is reduced to the minimum. This is because, when the patient is wearing the apparatuses 10a and 10b for protecting dental patient hearing, the body temperature of 30° C. or higher is measured through a temperature measuring module and contrary to this, when the apparatuses 10a and 10b are not worn, the body temperature of 30° C. or higher cannot be measured. Thus, when the patient does not wear the apparatuses 10a and 10b for protecting dental patient hearing, the current mode may be converted into the standby mode so that power can be saved. The apparatuses 10a and 10b converted into the standby mode starts a noise reduction function by stopping the standby mode when temperature above a preset temperature is detected through the temperature measuring module.

The connection portion 400 may be omitted from the earphone-type apparatus 10b for protecting dental patient hearing. In this case, when a pair of body portions 11b are spaced apart from each other by a preset distance or more, a warning message may be output through the speaker module 300 so that the apparatus 10b for protecting dental patient hearing may be prevented from being lost. Also, when the earphone-type apparatus 10b for protecting dental patient hearing includes an earplug, the earphone-type apparatus 10b for protecting dental patient hearing may be formed in a structure in which an earplug and the speaker module 300 are detachably attached to each other. In this case, when a plurality of earplugs each having a preset size are provided, the earplug corresponding to the size of the ear of the user may be coupled to the speaker module 300 and used. Thus, when treatment of the patient ends, the used earplug may be replaced so that a hygienic environment for preventing infection between patients can be provided.

In the case of the headphone-type apparatus 10a for protecting dental patient hearing, the speaker module 300 and the connection portion 400 may be provided in various sizes so that a comfortable wearing sense can be provided to the patient. This is because the shapes or sizes of the ears of adult patients or pediatric patients are diversified.

In another alternative embodiment, power for driving the apparatus 10 for protecting dental patient hearing may be implemented with a battery or may be connected to the medical chair and supplied. When power for driving the apparatus 10 for protecting dental patient hearing is implemented in a battery manner, the power of the battery can be saved through the above-described standby mode.

In another alternative embodiment, the apparatus 10 for protecting dental patient hearing may be implemented to be connected to an additional set top box. In this case, a wired/wireless function may be additionally included in the apparatus 10 for protecting dental patient hearing, and a monitor display portion is provided to the patients' view so that the apparatus 10 for protecting dental patient hearing may be provided in a shape like driving an application of a smartphone. This allows the extension of the function for collecting noise inside a program or application of the set top box, a section for storing data of existing noise, and a function for recommending music suitable for the range of noise. Also, the apparatus 10 for protecting dental patient hearing may be developed as a smartphone or an earphone-connected product and sold.

In addition, the apparatus 10 for protecting dental patient hearing further includes a sensor for measuring biodata such as a heartbeat in addition to the temperature measuring module so as to check the state of the patient. For example, a heartbeat sensor may measure the degree of tension/excitement of the patient and may be used for simple measurement of high blood pressure patients above BP 140 or for preparation for an emergency. The patient's biodata measured in this way may be prepared in a shape to be transmitted and received for being stored in a portable terminal device in real time, and may be implemented so that a monitor provided in a ward can check these information in real time. Also, the degree of tension or excitement of the user may be measured based on at least one of temperature and heart rate measured by the temperature measuring module and the heartbeat sensor so that, when recognizing an emergency (when it is recognized to be higher or less than a preset temperature value or heart rate), an alarm signal may also be generated.

While the present invention has been particularly shown and described with reference to exemplary embodiments thereof, it will be understood by those of ordinary skill in the art that various changes in form and details may be made therein without departing from the spirit and scope of the present invention as defined by the following claims.

The invention claimed is:

1. An apparatus for protecting dental patient hearing through noise reduction, the apparatus comprising:
   a main body portion provided in a form that can be mounted on both ears of a user;
   a microphone module that is provided on one side of the main body portion and collects external sound signals generated from the outside;
   a noise filter module that is built in the main body portion and filters the external sound signals to block or reduces noise signals included in the external sound signals; and
   a speaker module that is built in the main body portion and provided on the other side of the main body portion corresponding to the ears of the user, and that outputs sound signals filtered by the noise filter module,
   wherein a temperature measuring module is further provided inside the main body portion to measure a temperature of a user in real time, and when the temperature is measured to be less than a preset value, a current mode is converted into a standby mode in which an operation of the main body portion is stopped and power consumption is reduced to minimum.

2. The apparatus of claim 1, wherein a low pass filtering technology for blocking or reducing sound above a preset filtering reference frequency is applied to the noise filter module.

3. The apparatus of claim 1, wherein the noise filter module is configured to determine sound that satisfies one or more conditions among frequency conditions above a filtering reference frequency and level conditions above a filtering reference sound level, as the noise signals.

4. The apparatus of claim 1, wherein, when the main body portion is connected to an external storage device, a first sound signal received from the external storage device is output through the speaker module and a second sound signal above a preset level of the output of the first sound signal is additionally received, the first sound signal being output is stopped, or a volume of the first sound signal is reduced by a preset value.

5. The apparatus of claim 4, wherein the first sound signal is stopped, or a volume of the first sound signal is reduced by a preset value and simultaneously, the second sound signal filtered through the noise filter module is output through the speaker module.

6. The apparatus of claim 1, wherein, when preset white noise is output through the speaker module and a sound signal is received through the microphone module, an output of the white noise is stopped.

7. The apparatus of claim 1, wherein a heartbeat sensor is provided inside the main body portion, and a degree of the user's tension or excitement is measured based on at least one of temperature and heart rates measured by the temperature measuring module and the heartbeat sensor to generate an alarm signal when an emergency is recognized.

8. The apparatus of claim 7, wherein, when temperature above a preset temperature is sensed through the temperature measuring module of the main body portion converted into the standby mode, the standby mode is stopped.

9. The apparatus of claim 1, further comprising a main body portion corresponding to both ears, and a connection portion for connecting the main body portion, wherein the microphone module is mounted on the connection portion, and the microphone module and the speaker module have a structure in which the microphone module and the speaker module are spaced apart from each other by a preset length.

10. The apparatus of claim 1, further comprising an earplug detachably coupled to the speaker module.

11. The apparatus of claim 10, wherein a plurality of earplugs each having a preset size are provided, and an earplug having a size corresponding to a size of the user's ear among the plurality of earplugs is coupled to the speaker module.

12. The apparatus of claim 1, wherein the main body portion is connected to an external microphone device, directly receives a sound signal generated through the external microphone device and outputs the sound signal to the speaker module.

13. The apparatus of claim 1, wherein a sound signal in which a first sound signal and a second sound signal are mixed, is received from a transmitter worn by a medical staff together with an external microphone, the first sound signal is a sound signal included in content stored in an external device, and the second sound signal is a sound signal received through the external microphone.

14. The apparatus of claim 1, wherein a sound signal in which a first sound signal and a second sound signal are mixed, is received from a transmitter worn by a medical staff together with an external microphone, the first sound signal is a sound signal included in content stored in the transmitter, and the second sound signal is a sound signal received through the external microphone.

15. The apparatus of claim 14, wherein a sound signal in which a first sound signal and a second sound signal are mixed, is received from an external terminal device, the first sound signal is a sound signal included in content stored in the external terminal device, and the second sound signal is a sound signal received through the external microphone and transmitted to the external terminal device.

16. An apparatus for protecting dental patient hearing through noise reduction, the apparatus comprising:
   a main body portion provided in a form that can be mounted on both ears of a user;
   a microphone module that is provided on one side of the main body portion and collects external sound signals generated from the outside;

a noise filter module that is built in the main body portion and filters the external sound signals to block or reduces noise signals included in the external sound signals; and a speaker module that is built in the main body portion and provided on the other side of the main body portion corresponding to the ears of the user, and that outputs sound signals filtered by the noise filter module, wherein the main body portion is provided as a pair of earphone types to correspond to the user's ear, and when a pair of main body portions are spaced apart from each other by a preset distance or more, a warning message is output through the speaker module.

* * * * *